United States Patent [19]
Lin et al.

[11] Patent Number: 5,719,132
[45] Date of Patent: Feb. 17, 1998

[54] COMPOSITIONS AND METHODS OF TREATING HIV WITH D4T, 5-FLUOROURACIL/TEGAFUR, AND URACIL

[75] Inventors: Pin-Fang Lin, Branford; Yi-Fei Gong, Rocky Hill, both of Conn.

[73] Assignee: Bristol-Myers Squibb Company, Princeton, N.J.

[21] Appl. No.: 671,476

[22] Filed: Jun. 27, 1996

[51] Int. Cl.$^6$ .................. C07H 19/073; A01N 43/54; A61K 31/505; A61K 31/70
[52] U.S. Cl. .................. 514/50; 514/274; 536/28.55; 544/309; 544/310; 544/313
[58] Field of Search .................. 514/50, 274; 536/28.55; 544/309, 310, 313

[56] References Cited

U.S. PATENT DOCUMENTS

| | | | |
|---|---|---|---|
| 3,948,897 | 4/1976 | Townsend et al. | 544/313 |
| 4,328,229 | 5/1982 | Fujii et al. | 514/274 |
| 4,507,301 | 3/1985 | Fujii et al. | 514/274 |
| 4,724,232 | 2/1988 | Rideout et al. | 514/50 |
| 4,861,759 | 8/1989 | Mitsuya et al. | 514/46 |
| 4,863,902 | 9/1989 | Amagase et al. | 514/12 |
| 4,978,655 | 12/1990 | Lin et al. | 514/50 |
| 5,116,823 | 5/1992 | Calabresi et al. | 514/50 |
| 5,521,161 | 5/1996 | Malley et al. | 514/45 |
| 5,525,603 | 6/1996 | Shirasaka et al. | 514/241 |
| 5,530,003 | 6/1996 | Yanagawa | 514/256 |
| 5,534,513 | 7/1996 | Junji et al. | 514/249 |

FOREIGN PATENT DOCUMENTS

| | | |
|---|---|---|
| 870982 | 2/1979 | Belgium . |
| 4151988 | 11/1979 | Japan . |
| 58-38210 | 3/1983 | Japan . |
| 61-34428 | 8/1986 | Japan . |
| 136442 | 7/1989 | Japan . |
| 436237 | 2/1992 | Japan . |
| 848635 | 2/1996 | Japan . |
| 9117660 | 11/1991 | WIPO . |
| 9301202 | 1/1993 | WIPO . |
| WO93/01202 | 1/1993 | WIPO . |
| 9426761 | 11/1994 | WIPO . |
| WO94/27590 | 12/1994 | WIPO . |
| 9512400 | 5/1995 | WIPO . |
| 9628162 | 9/1996 | WIPO . |

OTHER PUBLICATIONS

S.D. Malley, et al, "Suppression of HIV Production in Resting Lymphocytes by Combining Didanosine and Hydroxamate Compounds," The Lancet, vol. 343, p. 1292, May 21, 1994.

M.R. Posner, et al, "High–Dose Intravenous Zidovudine with 5–Fluorouracil and Leucovorin," Cancer, vol. 70, No. 12; pp. 2929–2934, Dec. 15, 1992.

S.A. Riddler, et al, "Antiretroviral Activity of Stavudine (2',3'-Didehydro–3'-Deoxythymidine, D4T)," Antiviral Research, vol. 27, pp. 189–203, 1995.

P.F. Lin, et al, "Genotypic and Phenotypic Analysis of Human Immunodeficiency Virus Type 1 Isolates from Patients on Prolonged Stavudine Therapy," J. Infect. Dis., vol. 170, pp. 1157–1164, 1994. (November).

W.-Y. Gao, et al, "Anti–Human Immunodeficiency Virus Type 1 Activity of Hydroxyurea in Combination with 2',3'-Dideoxynucleosides," Mol. Pharm., vol. 46, pp. 767–772, 1994.

F. Lori, et al, "Hydroxyurea as an Inhibitor of Human Immunodeficiency Virus–Type 1 Replication," Science, vol. 266, pp. 801–805, (Nov. 4, 1994).

V.A. Johnson and R.E. Byington, "Quantitative Assays for Virus Infectivity," in A. Aldovini and B.D. Walker (Ed.), Techniques in HIV Research, Stockton Press, New York, pp. 71–76, 1990.

S, Cox, et al, "Comparison of the Intracellular Metabolism of 3'-Azido–3'-Deoxythymidine and 3'-Fluoro–3'-Deoxythymidine in Lymphocytes in the Presence of 5-Fluoro–2'-Deoxyuridine," Antiviral Chemistry and Chemotherapy, vol. 1, No. 2, pp. 155–161, 1990.

W.-Y. Gao, et al, "Low Levels of Deoxynucelotides in Peripheral Blood Lymphocytes: A Strategy to Inhibit Human Immunodeficiency Virus Type 1 Replication," Proc. Natl. Acad. Sci., vol. 90, pp. 8925–8928, Oct., 1993.

J. Balzarini, et al, "2',3'-Dideoxycytidine: Regulation of its Metabolism and Anti-Retroviral Potency by Natural Pyrimidine Nucleogide Synthesis, and by Inhibitors of Pyrimidine Nucleotide Synthesis" Molecular Pharmacology, vol. 32, No. 6, pp. 798–806, Dec., 1987.

M.N. Prichard, et al, "Inhibition of Thymidylate Synthase and Dihydrofolate Reductase Potentiate the Antiviral Effect of Acyclovir," Antiviral Research, vol. 20, pp. 249–259, 1993.

F. Lori, et al, "Hydroxyurea Inhibits HIV–1 Replication by Inducing Low dNTP Levels. A Cellular Enzyme as a Target to Inhibit HIV–1," Antiviral Research, vol. 23, p. 63, 1994.

W.-Y. Gao, et al, "Anti–HIV 1 Activity of Hydroxyurea in Combination with 2',3'-Dideoxynucleosides," Clinical Research, vol. 42, No. 2, p. 280A, 1994.

Gong et al., "Potentiation of the Stavudine Anti–Human Immunodeficiency Virus Activity by 5–Fluorouracil," *Antimicrobial Agents & Chemotherapy*, 40(5), 1229 (May 1996).

Vila et al, "Absence of Viral Rebound After Treatment of HIV–Infected Patients with Didanosine [ddI] and Hydroxycarbamide [Hydroxyurea]," *Lancet*,350(9078), 635–636 (Aug. 30, 1997).

*Primary Examiner*—John Kight
*Assistant Examiner*—L. Eric Crane
*Attorney, Agent, or Firm*—Samuel J. DuBoff

[57] ABSTRACT

The present invention is directed to the use of pharmaceutical compositions containing anti-retroviral effective amounts of (a) d4T and (b) 5-fluorouracil or a prodrug, or salt thereof.

8 Claims, No Drawings

COMPOSITIONS AND METHODS OF TREATING HIV WITH D4T, 5-FLUOROURACIL/TEGAFUR, AND URACIL

BACKGROUND OF THE INVENTION

1. Field of the Invention

The present invention relates to a method for treating mammals, including human beings, infected with a retrovirus, such as HIV, with an anti-retroviral effective amount of (a) d4T and (b) 5-fluorouracil or a prodrug, or salt thereof.

2. Background Art

Acquired immunodeficiency syndrome (AIDS) is generally accepted to be a consequence of infection with the retrovirus variously termed human T-lymphotropic virus type III (HTLV-III), lymphadenopathy-associated virus (LAV), AIDS associated retrovirus (ARV), or human immunodeficiency virus (HIV). A number of compounds have demonstrated antiviral activity against this virus which include 2',3'-dideoxycytidine (ddC); azidothymidine (AZT); 2',3'-dideoxycytidin-2'-ene (d4C); 2',3'-dideoxyadenosine (ddA); 2',3'-dideoxyinosine (ddI); and 3'-deoxythymidin-2'-ene (d4T). See for example U.S. Pat. Nos. 4,861,759 to Mitsuya, et al (ddI), 4,978,655 to Lin, et al (d4T), and 4,724,232 to Burroughs Wellcome (AZT).

Pharmaceutical products for treating AIDS patients are currently available containing some of these compounds as the active ingredient such as Zerit® (contains d4T), Videx® (contains ddI), and Retrovir® (contains AZT). However, to date, these compounds or combinations thereof, have only proven to be effective in preventing the infection from spreading for relatively short durations of time (e.g. 6 months to 2-3 years) until drug resistance sets in. They have not resulted in long-term cures nor prevented death from ultimately occurring in patients.

Furthermore, such compounds have exhibited in human beings undesirable severe side effects and toxicities which have limited their usefulness. Such toxicities and side effects are for example anemia, bone marrow suppression, myositis, headaches, nausea, vomiting, malaise, seizures, peripheral neuropathy and pancreatitis.

There has also been mentioned the use of various combinations of the aforementioned drugs for treating AIDS, as well as the use of agents to potentiate either antiviral or anticancer activity of these drugs with some success to date. For example, the use of a known anticancer agent, hydroxyurea, in combination with ddI for suppressing HIV has been reported in *The Lancet*, vol. 343, May 21, 1994, p. 1292, by S. D. Malley, et al.

Also, PCT application WO 94/27590 to R. C. Gallo, et al, published Dec. 8, 1994, discloses the use of a compound that depletes the intracellular pool of deoxyribonucleoside phosphate (e.g. hydroxyurea) in combination with another antiviral such as ddI, AZT, ddC, etc. to inhibit HIV replication. There is no mention of antiviral compositions containing d4T with 5-fluorouracil or analogs thereof.

Additionally, the use of combinations of AZT with known anticancer agents such as 5-fluorouracil, 5-fluoro-2'-deoxyuridine or methotrexate has been reported for treating carcinomas in U.S. Pat. No. 5,116,823 to Calabresi, et al. Also, AZT with 5-fluorouracil and leucovorin as an anticancer agent has been reported in *Cancer*, Dec. 15, 1992, vol. 70, No. 12, pp. 2929–34. However, there is no mention of the use of these anticancer agents for potentiating the antiviral effect.

One of the most recent drugs to be approved in the U.S. for treating HIV-caused infection in humans is d4T (sold as Zerit®). Although further evaluation of the drug is ongoing, it is still desirable to further improve its duration of effectiveness and lower its undesirable side effects, including peripheral neuropathy.

SUMMARY OF THE INVENTION

It has now been surprisingly and unexpectedly found that compositions containing (a) d4T and (b) 5-fluorouracil or a prodrug, or salt thereof are more effective than d4T alone in treating retroviral infection, particularly HIV infection.

In one embodiment of the invention there is provided a method for treating mammals infected with a retrovirus, comprising administering to said mammal an anti-retroviral effective amount of a composition comprising (a) d4T and (b) 5-fluorouracil or a prodrug, or salt thereof.

In preferred embodiment the retrovirus is HIV.

In another preferred embodiment the prodrug comprises uracil and ftorafur and the amount of uracil present is from about 0.5 to 100 moles per mole of ftorafur or salt thereof.

In another preferred embodiment the amount of uracil present is 4 moles per mole of ftorafur.

In another preferred embodiment the composition comprises d4T and 5-fluorouracil.

In another embodiment of the invention there is provided a pharmaceutical composition comprising an anti-retroviral effective amount of (a) d4T and (b) 5-fluorouracil or a prodrug, or salt thereof.

In another preferred embodiment the prodrug comprises uracil and ftorafur and the amount of uracil present in the pharmaceutical composition is from about 0.5 to 100 moles per mole of ftorafur or salt thereof.

In another preferred embodiment the amount of uracil present is 4 moles per mole of ftorafur.

In another preferred embodiment the composition comprises an anti-retroviral effective amount of d4T and 5-fluorouracil.

DETAILED DESCRIPTION OF THE INVENTION

Stavudine, 2',3'-didehydro-3'-deoxythymidine (d4T), is a potent inhibitor of HIV-1 reverse transcriptase in vitro as reported by S. A. Riddler, et al in *Antiviral Research*, 1995, vol. 27, pp. 189–203. In clinical studies, stavudine has greater than 80% oral bioavailability and the dose-limiting toxicity is peripheral neuropathy. Stavudine treated patients have experienced increases in CD4 counts, and decreases in both serum p24 levels and infectious HIV titers in peripheral blood mononuclear cells (PBMC). Moreover, no resistant viruses can be isolated from 20 patients who have been treated with d4T for up to 24 months as reported by P. F. Lin, et al, in *J. Infect. Dis.*, 1994, vol. 170, pp. 1157–64. However, the duration of anti-viral responses is limited: CD4 counts and serum p24 levels return to baseline after approximately 6 months as reported by S. A. Riddler, et al. It was therefore desirable to search for compounds that may enhance the d4T antiviral activity in combination therapy.

The antiviral action of d4T relies on its intracellular conversion to the 5'-monophosphate (d4T—MP) by thymidine kinase (TK), followed by the formation of 5'-diphosphate and 5'-triphosphate (d4T—TP). The triphosphate is the active metabolite of d4T, since incorporation of d4T—TP into viral DNA by reverse transcriptase results in viral death. In fact, anti-HIV activity of d4T depends on the ratio of d4T—TP to dTTP because dTTP functions as a competitive substrate of reverse transcriptase. The key step involved in endogenous synthesis of deoxythymidine triphosphate (dTTP) is the conversion of deoxyuridine monophosphate (dUMP) to deoxythymidine monophosphate (dTMP) by thymidylate synthetase (TS) with dTTP also serving as a feedback inhibitor of TK. Since thymidylate synthetase inhibitors can potentially exert two effects on the d4T activity, a reduction of endogenous dTTP level and an increase in d4T—TP as a consequence of TK enhancement by a low dTTP concentration, it was theorized that this class of inhibitors may potentiate the antiviral effect of d4T. A similar rationale has been successfully applied to ddI, which showed that lowering the endogenous levels of deoxyadenosine triphosphate (dATP), an active metabolite of ddI, by hydroxyurea yield an enhanced anti-HIV activity of ddI as reported by W. Gao, et al. in *Mol. Pharm.*, 1994, vol. 46, pp. 767–72; F. Lori, et al, *Science*, 1994, vol. 266, pp. 801–05; and S. D. Malley, et al mentioned previously. It is noted, however, that such potentiating effect by hydroxyurea was only reported as being good for ddI, and not for other nucleosides such as ddC or AZT.

5-fluorouracil (5-FU) is an anti-neoplastic agent used in the palliative treatment of various adenocarcinomas and has the structure (I) below:

5-Fluorouracil (5-FU)

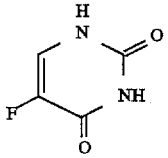

(I)

Since this compound functions as an effective TS inhibitor, the effect of 5-FU on the d4T antiviral activity was investigated. Fluorouracil alone (up to 0.5 µM) exhibits no antiviral activity in phytohemagglutinin (PHA)-activated peripheral blood mononuclear cells (PHA—PBMC) acutely infected by a clinical HIV isolate called JEW. The 50% cytotoxicity concentration of 5-FU in PHA—PBMC is approximately 9 µM (i.e. micromolar) as determined by trypan blue staining. Using this clinical isolate, it was surprisingly found that inclusion of 0.5 µM of 5-FU can stimulate (i.e. fold enhancement) the anti-HIV activity of d4T by as much as 4-fold as shown in the results of Table 1. In separate experiments, using a different clinical HIV isolate called OLR, a 4.5 fold enhancement of d4T activity in PBMC by 0.1 µM of 5-FU was observed. However, parallel experiments reveal that 5-FU has no potentiating effect on the anti-HIV activity of ddI, as shown in Table 2.

Importantly, the active concentration of 5-FU (up to 0.5 µM) is non-toxic to PBMC and has no potentiating effect on d4T cytotoxicity. Moreover, its active concentration is lower than those currently used in human therapy and the toxicity profiles of d4T and 5-FU are non-overlapping (i.e. do not affect the same body tissue or organs).

TABLE 1

Enhancement of d4T Anti-HIV Activity in PHA-Stimulated PBMC

| 5-FU Concentration (µM) | $EC_{50}$ (nM) of d4T[a] | Fold Enhancement |
|---|---|---|
| 0 | 98 ± 42 | — |
| 0.2 | 92 ± 39 | 1 X |
| 0.5 | 27 ± 15 | 4 X |

TABLE 2

Effect of 5-FU on ddI Anti-HIV Activity in PHA-Stimulated PBMC

| 5-FU Concentration (µM) | $EC_{50}$ (nM) of ddI[a] | Fold Enhancement |
|---|---|---|
| 0 | 100 ± 32 | — |
| 0.2 | 170 ± 2 | 0.6 X |
| 0.5 | 138 ± 26 | 0.7 X |

In the Tables 1, 2 and hereinafter, the following definitions apply.
- "µM" means micromolar and equals 1,000 nM;
- "nM" means nanomolar;
- "ng" means nanograms;
- "mM" means millimolar;
- "ml" means milliliter;
- "Kg means kilograms;
- "a" refers to the $EC_{50}$ data as representing the mean values from three experiments, with duplicate determinations in each experiment.

The materials and experimental procedure used to obtain the results reported in Tables 1 and 2 are described below.

Cells—Peripheral blood mononuclear cells (PBMC) from normal individuals were prepared by Ficoll-Hypaque gradient centrifugation of venous blood with citrate as an anticoagulant and stimulated with phytoagglutinin (PHA—P, 4 µg/ml, Sigma Chemical, St. Louis, Mo.) and interleukin-2 (IL-2, 1 ng/ml, Upstate Biotechnology Inc., Lake Placid, N.Y.) for three days.

Virus—A clinical HIV-1 isolate, JEW, was titrated with a infectivity assay [Johnson, V. A. and R. E. Byington. 1990. Infectivity assay, p. 71–76. in A. Aldovini and B. D. Walker (ed.), Techniques in HIV Research. Stockton Press, New York], and used in our experiments.

Chemicals—d4T was supplied by Bristol-Myers Squibb Company. 5-Fluorouracil (5-FU) was purchased from Sigma.

Experiment
1. PBMC were infected by the clinical isolate JEW at a multiplicity of infection (MOI) of 0.001 at 37° C. for one hour, and then resuspended in RPMI 1640 medium (Gibco, Gaithersburg, Md.) containing 20% fetal bovine serum (FBS, Sigma), 1 ng/ml IL-2 and 2 mM L-glutamine (Gibco) at a concentration of 4×10⁶ cells/ml.
2. d4T (2 µM) or ddI (40 µM) was serially diluted 1:3 into RPMI 1640 medium with a final volume of 100 µl/well in 96-well plates, and 50 µl of 2.0 µM, 0.8 µM and 0 µM 5-FU were then added to each well.
3. 50 µl of 4×10⁶/ ml infected PBMC were added to each well in these plates to get a final 1×10⁶ cells/ml, and incubated at 37° C.
4. Half media (100 µl) from each well were removed and replaced with fresh medium containing same concentrations of drug at day 3 or 4.

5. Samples were collected at day 7 and the p24 levels were quantitated using a HIV p24 ELISA kit (Dupont, Boston, Mass.).
6. The 50% effective concentration ($EC_{50}$) was calculated as the concentration of drug that decreased the percentage of p24 production in drug-treated cells to 50% of that produced by untreated cells.
7. To determine the cytotoxicity of 5-FU, uninfected PBMC were incubated with a series of concentrations of 5-FU (i.e., 0.04, 0.16, 0.63, 2.5 and 10 µM). To determine whether 5-FU can affect the cytotoxicity of d4T, uninfected PBMC were incubated with a series of concentrations of d4T (i.e., 0.8, 3.1, 12.5, 50 and 200 µM) containing 0.02 µM of 5-FU. This was repeated with d4T using 5-FU concentrations of 0.1 µM and 0.5 µM, respectively. Cell viability was monitored by trypan blue exclusion assay. Results were expressed as a percentage of living cells in drug testing wells compared to those in untreated control wells. The 50% cytotoxic concentration ($CC_{50}$) was calculated as the concentration of drugs that decreased the percentage of living cells in drug-treated wells to 50% of those in untreated wells.

It is also contemplated within the scope of the invention herein to be able to use in place of 5-fluorouracil in the d4T compositions disclosed, a prodrug which converts substantially to 5-fluorouracil in the body. Examples of such prodrugs are doxifluridine, floxuridine and mixtures of ftorafur and uracil (e.g. UFT).

The structural formulas for ftorafur (i.e. tegafur; 5-fluoro-1-(tetrahydro-2-furyl) uracil) and uracil are provided below as formulas (II) and (III) respectively:

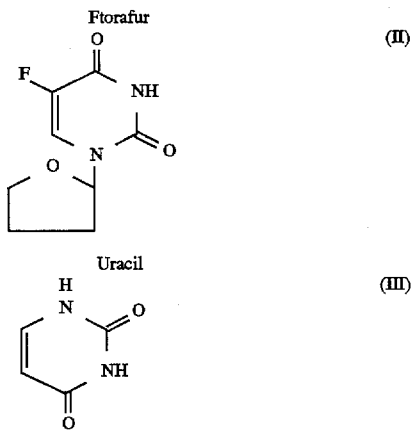

Such mixtures are described in more detail in U.S. Pat. Nos. 4,328,229 and 4,507,301 to Fuji, et al wherein useful molar ratios of uracil to ftorafur or salts thereof from about 0.5 to 100 are disclosed.

Although 5-FU has been available in injectable form, an orally-administered Japanese anticancer product called UFT, which is sold by Taiho Pharmaceutical Co. Ltd., can be used.

UFT is a mixture (molar ratio 4:1) of uracil and ftorafur. Ftorafur is an antineoplastic antimetabolite and uracil a naturally occurring base. Ftorafur (chemical name: tetrahydrofuryl-5-fluorouracil, also known as tegafur or Futraful™) is a fluorinated pyrimidine which acts as a slow-release prodrug of 5-fluorouracil, the active compound. Discovered in 1957, 5-fluorouracil is an antineoplastic antimetabolite widely used in the treatment of solid tumors, particularly of the gastrointestinal tract. Its mechanism of action is based on the observation that tumor cells utilize the base uracil for DNA synthesis more efficiently than normal cells. However, 5-fluorouracil has a very short half-life, and attempts to manage this limitation by introducing prolonged infusions of the compound and various biomodulators have been pursued. Ftorafur was synthesized in 1967 at the Institute of Chemistry of Riga (Latvia) and is believed to be activated to 5-fluorouracil by liver enzymes. Ftorafur is currently marketed in Japan, as well as in several other countries in Europe, as an intravenous formulation and, in some countries, as an orally active compound. Investigators in Japan found that uracil strongly inhibits the degradation of 5-fluorouracil in vitro and that co-administration of uracil and ftorafur in vivo results in a greater concentration of 5-fluorouracil in tumors as compared to ftorafur or 5-fluorouracil.

Pharmaceutical compositions according to the invention herein are generally described for the individual components, d4T in U.S Pat. No. 4,978,655 and for 5-fluorouracil or combinations of ftorafur and uracil in U.S. Pat. Nos. 4,328,229 and 4,507,301. Suffice it to say that these compositions can be administered individually or together, orally in the form of tablets, capsules, granules, liquids, etc., by injection or other routine form of administation. They are formulated by usual methods using excipients or carriers heretofore used in the art.

In practicing the invention, (a) d4T and (b) 5-FU, or a prodrug, or salt thereof may be mixed together and administered simultaneously, either by intravenous or intra-arterial injection or orally where possible in any conventional carrier or vehicle such as normal saline or 5% aqueous dextrose solution, or in any other non-toxic pharmacologically acceptable vehicle or carrier. Alternatively, each component may be administered separately provided they are spaced apart by no more than about 48 hours, preferably by less than about 6 hours. In general, the less time elapsing between administration of the two components the better.

The relative proportions of the two components may be varied over a wide range such as, but not limited to, from about 0.5 to 20 parts by moles of 5-FU or a prodrug, for each part of d4T.

The dosage may also vary over a wide range, the upper limit being generally determined by the toxicity of the components. The toxicity of all of the components when used individually has long been known and is not greatly changed by using both components together. However, while the standard dose of d4T has been 1–1.333 mg/kg/day according to the prior art, the dose for humans in the present invention may be varied due to the potentiating or synergistic effect of 5-FU or a prodrug thereof. In the case of 5-FU, the dose for humans according to the prior art is 12 mg/kg/day, with the maximum not to exceed 800 mg/day during a course of therapy. At least one week must be allowed as a rest period, preferably two weeks, between courses of therapy.

As for prodrugs of 5-FU, the same dosage levels as for 5-FU would be expected to apply.

Also, contemplated within the scope of the invention are salts of d4T, 5-FU or prodrugs thereof, that are pharmacologically acceptable. Typical of such salts are the alkali metal salts, especially the sodium salt and the potassium salt.

What is claimed is:

1. A method for treating mammals infected with HIV, and in need thereof, comprising administering to said mammal a therapeutically effective amount of a composition selected from the group consisting of:
   (a) d4T and 5-fluorouracil;
   (b) d4T, tegafur and uracil, wherein the amount of uracil present is 4 moles per mole of tegafur; and
   (c) pharmaceutically acceptable salts thereof.

2. The method of claim 1 wherein said composition is (a).
3. The method of claim 1 wherein said composition is (b).
4. The method of claim 1 wherein said composition is (c).
5. A pharmaceutical composition selected from the group consisting of:
   (a) d4T and 5-fluorouracil;
   (b) d4T, tegafur and uracil, wherein the amount of uracil present is 4 moles per mole of tegafur; and
   (c) pharmaceutically acceptable salts thereof.
6. The composition of claim 5 wherein said composition is (a).
7. The composition of claim 5 wherein said composition is (b).
8. The composition of claim 5 wherein said composition is (c).

* * * * *